United States Patent
Martin et al.

(10) Patent No.: US 7,373,700 B2
(45) Date of Patent: May 20, 2008

(54) SKIN-FRIENDLY HOOK FASTENING COMPONENT

(75) Inventors: Timothy R. Martin, Alpharetta, GA (US); Alexander J. Neeb, Alpharetta, GA (US); Richard J. Schmidt, Roswell, GA (US); Brian Vanbenschoten, Rochester, NH (US); Heidi Tremblay, Windham, NH (US); Christopher M. Gallant, Nottingham, NH (US); Scott M. Filion, Newmarket, NH (US); Keith G. Buzzell, North Waterboro, ME (US); Joseph K. Parshley, Salem, MA (US)

(73) Assignee: Velcro Industries B.V., Curacao (AN)

( * ) Notice: Subject to any disclaimer, the term of this patent is extended or adjusted under 35 U.S.C. 154(b) by 0 days.

(21) Appl. No.: 11/622,840

(22) Filed: Jan. 12, 2007

(65) Prior Publication Data
US 2007/0137007 A1 Jun. 21, 2007

Related U.S. Application Data

(63) Continuation of application No. 09/793,057, filed on Feb. 26, 2001, now Pat. No. 7,162,780.

(51) Int. Cl.
*A44B 18/00* (2006.01)
*A61F 13/62* (2006.01)
*A61F 13/56* (2006.01)
(52) U.S. Cl. .................. 24/452; 428/100; 604/391
(58) Field of Classification Search ............ 24/452; 428/100; 604/391
See application file for complete search history.

(56) References Cited

U.S. PATENT DOCUMENTS

| 3,408,705 | A | | 11/1968 | Kayser et al. |
| 3,717,908 | A | | 2/1973 | Perina |
| 4,056,593 | A | | 11/1977 | de Navas Albareda |
| 4,617,214 | A | * | 10/1986 | Billarant ............ 428/40.1 |
| 4,726,975 | A | * | 2/1988 | Hatch ............... 428/100 |
| 4,842,916 | A | | 6/1989 | Ogawa et al. |
| 4,931,344 | A | * | 6/1990 | Ogawa et al. ......... 428/100 |
| 4,946,527 | A | | 8/1990 | Battrell |
| 4,984,339 | A | | 1/1991 | Provost et al. |

(Continued)

FOREIGN PATENT DOCUMENTS

CA 2278867 A1 3/2000

(Continued)

*Primary Examiner*—Robert J. Sandy
(74) *Attorney, Agent, or Firm*—Fish & Richardson P.C.

(57) ABSTRACT

A skin-friendly hook component of a hook and loop fastener that reduces or eliminates the occurrence of red-marking and/or irritation if brought into contact with a wearer's skin. In one embodiment, the hook component can have a relatively large top surface area among the hooks with respect to a surface area of the hook backing. In another embodiment, the hook backing is highly flexible, attributable to a flexible resin and/or modified topography. In yet another embodiment, a highly flexible polymer, or polymers, can be used to make individual hooks such that the hooks bend in response to a minimum amount of pressure. Various illustrated hook tapes have features along their edges to enhance skin-friendliness. A skin-friendly hook component results any combination of the disclosed embodiments. The hook component is particularly beneficial when used in absorbent articles.

13 Claims, 8 Drawing Sheets

U.S. PATENT DOCUMENTS

| | | |
|---|---|---|
| 5,019,073 A | 5/1991 | Roessler et al. |
| 5,067,210 A | 11/1991 | Keyaki |
| 5,318,555 A | 6/1994 | Siebers et al. |
| 5,392,498 A | 2/1995 | Goulait et al. |
| 5,398,387 A | 3/1995 | Torigoe et al. |
| 5,470,417 A | 11/1995 | Goulait |
| 5,549,591 A | 8/1996 | Landvogt |
| 5,678,286 A | 10/1997 | Murasaki |
| 5,692,271 A | 12/1997 | Provost et al. |
| 5,749,849 A | 5/1998 | Engelson |
| 5,755,015 A | 5/1998 | Akeno et al. |
| 5,781,969 A | 7/1998 | Akeno et al. |
| 5,786,061 A * | 7/1998 | Banfield ............... 428/100 |
| 5,792,408 A | 8/1998 | Akeno et al. |
| 5,813,095 A | 9/1998 | Robertson |
| 5,851,467 A | 12/1998 | Murasaki |
| 5,860,194 A | 1/1999 | Takizawa et al. |
| 5,891,549 A | 4/1999 | Beretta et al. |
| 5,900,303 A * | 5/1999 | Billarant ............... 428/100 |
| 5,930,876 A | 8/1999 | Takizawa et al. |
| 5,933,927 A | 8/1999 | Miller et al. |
| 5,942,177 A | 8/1999 | Banfield |
| 5,945,193 A | 8/1999 | Pollard et al. |
| 5,953,797 A | 9/1999 | Provost et al. |
| 5,964,742 A | 10/1999 | McCormack et al. |
| 5,985,407 A | 11/1999 | Murasaki |
| 6,000,106 A | 12/1999 | Kampfer et al. |
| 6,054,091 A | 4/2000 | Miller et al. |
| 6,061,881 A | 5/2000 | Takizawa et al. |
| 6,077,255 A | 6/2000 | Hunter et al. |
| RE36,779 E * | 7/2000 | Takizawa et al. ............. 24/452 |
| 6,106,922 A | 8/2000 | Cejka et al. |
| 6,180,205 B1 | 1/2001 | Tachauer et al. |
| 6,209,177 B1 | 4/2001 | Murasaki |
| 6,221,960 B1 | 4/2001 | Rajagopalan |
| 6,254,304 B1 | 7/2001 | Takizawa et al. |
| 6,849,142 B1 | 2/2005 | Goulait |

FOREIGN PATENT DOCUMENTS

| | | |
|---|---|---|
| EP | 0 766 934 A2 | 4/1997 |
| EP | 0 768 074 A1 | 4/1997 |
| EP | 0 800 379 B1 | 12/1999 |
| GB | 2 296 423 B | 7/1996 |
| WO | WO 93/00215 | 7/1993 |
| WO | WO 96/19960 | 7/1996 |
| WO | WO99/03369 | 1/1999 |

* cited by examiner

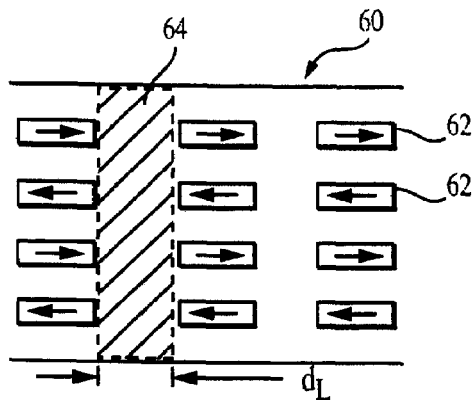
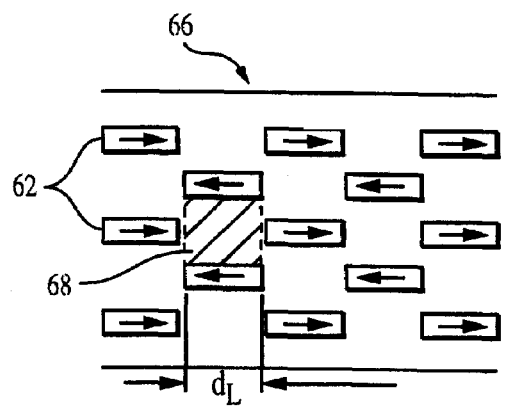
FIG. 12  FIG. 12A
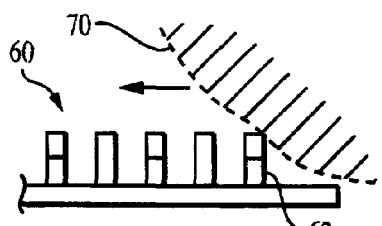
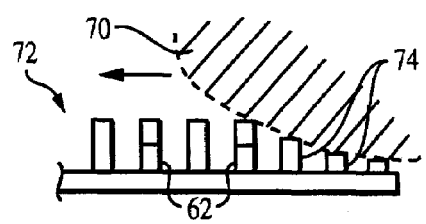
FIG. 13
PRIOR ART
FIG. 14
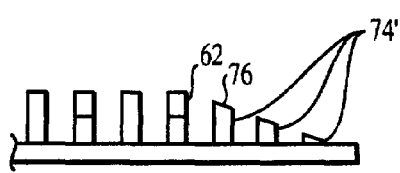
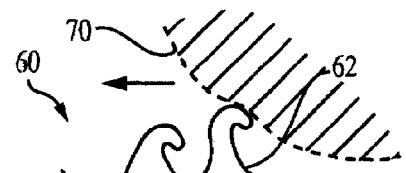
FIG. 15
FIG. 16
PRIOR ART
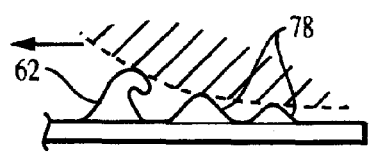
FIG. 17

SKIN-FRIENDLY HOOK FASTENING COMPONENT

CROSS-REFERENCE TO RELATED APPLICATIONS

This application is a divisional of and claims priority under 35 U.S.C. §121 to U.S. application Ser. No. 09/793,057, filed on Feb. 26, 2001, the entire contents of which are hereby fully incorporated by reference.

TECHNICAL FIELD

This invention is directed to a hook component of a hook and loop fastener. More particularly, the hook component reduces skin irritation typically caused by most hook components.

BACKGROUND

A number of fastening systems, such as diaper fastening systems, incorporate a hook and loop system for easy fastening and release. The hook component typically includes a flat plastic sheet laminate with a number of protruding hooks that engage with a number of loops on a loop component. The protruding hooks and rigid, flat, plastic backing of the hook component can produce red-marking and irritation if brought into contact with a person's skin, such as an infant's skin in contact with a hook component of a diaper fastening system.

Improvements to hook and loop fasteners often dwell on performance, such as improved engagement or maximized peel and shear strength. However, such improvements do not eliminate the problem of skin irritation.

There is a need or desire for a hook component of a hook and loop fastener that reduces or eliminates the occurrence of red-marking and/or irritation if brought into contact with a person's skin.

SUMMARY

The present invention is directed to a skin-friendly hook component of a hook and loop fastener. In one embodiment of the invention, the collection of hooks can have a large aspect ratio. In another embodiment of the invention, the hook component can have a highly flexible hook backing. In yet another embodiment of the invention, the hook component can be made of a highly flexible polymer. Any of these improvements to the hook component, or a combination of these improvements, result in a skin-friendly hook component that is soft to the touch and reduces or eliminates the occurrence of red-marking and/or irritation if brought into contact with a person's skin.

More particularly, hook components having a large percentage of hook aspect ratio, in relation to surface area of the hook component backing, reduce the threat of skin irritation compared to hook components having a small percentage of hook aspect ratio coverage. Hook aspect ratio maximization can be achieved through a combination of individual hooks having large aspect ratios and a relatively high density of hooks on the hook component.

Flexible hook backing material is also beneficial in terms of skin-friendliness. Flexible material can bend in response to pressure, thereby not poking a wearer with hooks the way rigid hook backings do. One method of making the hook backing more flexible is by reducing its thickness. The topography of the hook backing material can also be optimized to create regions of varying thicknesses or apertures that contribute to a highly flexible hook backing. The hook backing may also be made from a flexible polymer.

A hook component made of a highly flexible polymer can flex and bend correspondingly with a wearer's movements, both at a large flat-tape scale, and also at a small micro-hook level. Due to the flexibility, edges of the hook component are less likely to poke the wearer. Also, each individual hook bends in response to pressure, thereby alleviating stresses that could lead to skin irritation.

A hook component made of a highly flexible polymer, and/or with a highly flexible backing, and/or having a collection of hooks with a large aspect ratio significantly reduces skin irritation due to the greatly reduced stress responses to pressure.

With the foregoing in mind, it is a feature and advantage of the invention to provide a hook component of a hook and loop fastener that reduces or eliminates the occurrence of red-marking and/or irritation if brought into contact with a person's skin.

This hook component is particularly suitable for use in fastening systems on disposable absorbent articles. Examples of such suitable articles include diapers, training pants, feminine hygiene products, incontinence products, other personal care or health care garments, including medical garments, or the like.

The invention features an improved hook component for use with a mating loop component for hook and loop fastening, the hook component including a hook backing and a plurality of hooks protruding from one side of the hook backing.

According to one aspect of the invention, the hook component has an overall aspect ratio, as defined herein, within a range of 40 to 55 percent (preferably, 45 to 50 percent; more preferably, about 47 percent).

For some applications, the hooks comprise a polymer selected from the group consisting of elastomeric thermoplastic polymers and metallocene catalyzed polymers.

The hooks are arranged on the hook backing, in some embodiments, in a density of 155 to 310 hooks per square centimeter (preferably, 186 to 279 hooks per square centimeter; more preferably, 202 to 248 hooks per square centimeter).

In some cases, the hooks are J-shaped and/or have heads of molded resin and/or have at least one flat lateral side.

According to another aspect of the invention, the hook backing has a non-uniform thickness with areas of greater thickness about the hooks and areas of lesser thickness between the hooks.

Preferably, the hook component has tapered edges about a periphery of the hook backing.

Preferably, at least a portion of the hook backing has a thickness in a range from a positive amount to 3.5 mils (88.9 microns), more preferably from 0.5 mil (12.7 microns) to 3.0 mils (76.2 microns), and most preferably from 1.0 mil (25.4 microns) to 2.5 mils (63.5 microns).

The hook backing may be provided with a knurled texture on at least one surface, or apertures therethrough, for improved flexibility.

According to another aspect, a plurality of the hooks each have at least one rounded free end, and each of the hooks comprises a polymer having a bulk flexural modulus in a range of 7 kpsi (48 MPa) to 30 kpsi (207 Mpa), preferably 7 kpsi (48 MPa) to 25 kpsi (173 Mpa), and more preferably 7 kpsi (48 MPa) to 15 kpsi (104 MPa).

In some embodiments, the hook backing comprises a polymer having a bulk flexural modulus in a range of 7 kpsi (48 MPa) to 90 kpsi (621 Mpa), preferably 7 kpsi (48 MPa) to 70 kpsi (483 Mpa), and more preferably 7 kpsi (48 MPa) to 50 kpsi (345 MPa).

According to another aspect of the invention, the hook component usefully includes more than one feature of the invention for improved skin-friendliness. In one such combination, the hook component has an overall aspect ratio within a range of 20 to 55 percent, the hook backing has a non-uniform thickness with areas of greater thickness about the hooks and areas of lesser thickness between the hooks, and each of the hooks comprises a polymer having a bulk flexural modulus in a range of 7 kpsi (48 MPa) to 30 kpsi (207 Mpa).

According to another aspect, the hook component includes at least one row of edge transition members protruding from the backing between one longitudinal edge of the backing and the array of hooks, the edge transition members being of a height less than the nominal height of the hooks. Preferably, at least two rows of edge transition members protrude from the backing between the longitudinal edge and the array of hooks, with the edge transition members of an outer row being of a lesser height than the edge transition members of an inner row disposed between the hooks and the outer row of edge transition members. More preferably, three rows of edge transition members protrude from the backing between the longitudinal edge and the array of hooks, with the edge transition members of each row being taller than the members of any transition members closer to the longitudinal edge.

In some embodiments, the edge transition members are of molded form, and/or have upper surfaces angled away from the nearby longitudinal edge.

According to another aspect, the hook component includes at least one row of end transition members protruding from the backing between one end of the backing and the array of hooks, with the edge transition members being of a height less than the nominal height of the hooks. Preferably, at least two rows of end transition members (e.g., three rows) protrude from the backing between the end of the backing and the array of hooks, with the end transition members of an outer row being of a lesser height than the end transition members of an inner row disposed between the hooks and the outer row of end transition members.

According to yet another aspect, the hook component has an edge skirt protruding from the side of the backing between a longitudinal edge of the backing and the array of hooks. The skirt extends of a height greater than the nominal height of the hooks and is disposed sufficiently close to the array of hooks that when deflected toward the array of hooks the skirt extends over an upper edge of a closest row of hooks. Preferably, the edge skirt is integrally molded with the backing.

According to another aspect, the backing of the hook component is molded to form a V-shaped protrusion extending out of the plane of the backing toward the side of the backing from which the hooks protrude, with the V-shaped protrusion disposed between the array of hooks and an edge of the backing.

In another aspect of the invention, a laminate has a bottom layer laminated to a hook component for use with a mating loop component for hook and loop fastening. The hook component includes a generally planar hook backing and a plurality of hooks arranged in an array and protruding from a side of the hook backing opposite the bottom layer. Notably, as laminated, the backing of the hook component forms a discrete, V-shaped protrusion extending out of the plane of the backing away from the bottom layer, with the V-shaped protrusion disposed between the array of hooks and an edge of the backing.

In some preferred embodiments, the bottom layer extends beyond one longitudinal edge of the hook component for attaching the laminate to a garment (e.g., a diaper or another of the types of garments discussed above) to serve as a garment closure In some cases, the backing of the hook component is molded to form the V-shaped protrusion.

The invention also provides a method of forming a laminate hook component, the method including securing a hook tape to an underlying layer of material. The hook tape has a generally planar hook backing and a plurality of hooks arranged in an array and protruding from a side of the hook backing opposite the underlying layer of material, and the hook tape secured to the underlying layer of material in such a manner that the backing of the hook component forms a continuous protrusion extending out of the plane of the backing toward the side of the backing from which the hooks protrude, between portions of the backing secured to the underlying layer of material. The protrusion is disposed between the array of hooks and an edge of the backing.

In some applications the method includes, prior to securing the hook tape to the underlying layer of material, creasing the hook tape along spaced-apart hinge points to cause a portion of the backing to bend out of its plane for forming the protrusion.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10A shows the hook head area as the area of the upper face of the parallelepiped shown in dashed outline in FIG. 10.

FIG. 12 is a top view of a hook tape with the hooks of neighboring longitudinal rows aligned in the transverse direction.

FIG. 12A is a top view of a hook tape with the hooks of neighboring longitudinal rows staggered in the transverse direction.

FIG. 13 is an end view illustrating skin contact with an edge hook row of a prior art hook tape.

FIG. 14 is an end view illustrating skin contact with an edge of an improved hook tape with edge transition features.

FIG. 15 is an end view of an improved hook tape having a second form of transitional edge features.

FIG. 16 is a side view illustrating skin contact with a hook and the end of a prior art hook tape.

FIG. 17 is a side view illustrating skin contact with a hook and the end of an improved hook tape with end transitional features.

Like reference symbols in the various drawings indicate like elements.

DEFINITIONS

Figure 1:
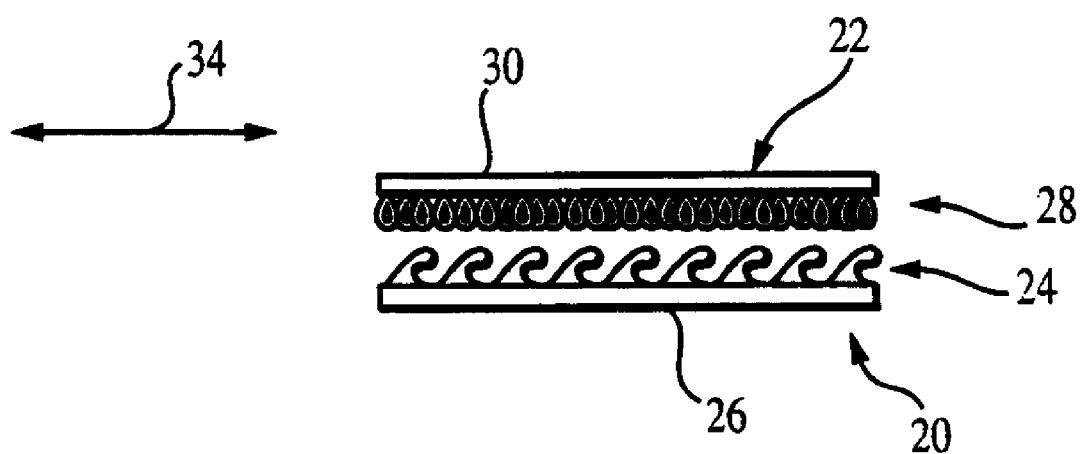
FIG. 1 is a front view of a hook component and a loop component prior to engagement with one another.

Within the context of this specification, each term or phrase below will include the following meaning or meanings.

"Aspect ratio" refers to the relative hook head density of a hook component. This ratio is related to the area of the engaging head of a hook that corresponds with the maximum instantaneous displaced area of a mating loop component as the hook head penetrates the loop component. In the context of the invention, it affects the feel of the hook component as the hook heads come into contact with a person's skin. The aspect ratio is measured as the aggregate hook head area divided by the overall area of the hook component. The hook head area is measured at an elevation above the hook backing that includes the maximum overhang of the hook head.

"Cross-machine direction" refers to a direction parallel with the hook backing and perpendicular to the lateral direction of maximum overhang of a hook. Mushroom-shaped hooks with equal overhang on all sides have no defined cross-machine direction.

"Flexible" refers to materials which are compliant and which will readily conform to the general shape and contours of the objects in contact with the materials.

"Machine direction" refers to a direction parallel with the hook backing in the lateral direction of maximum overhang of a hook, as opposed to "cross-machine direction" which refers to a direction generally perpendicular to the machine direction. Mushroom-shaped hooks with equal overhang on all sides have no defined machine direction.

"Medical garment" includes medical (e.g., protective and/or surgical) gowns, caps, gloves, drapes, face masks, blood pressure cuffs, bandages and the like.

"Non-pointed" refers to a surface that is blunt or smooth, and does not taper to a single point.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Thermoplastic" describes a material that softens when exposed to heat and which substantially returns to a non-softened condition when cooled to room temperature.

"Topography" refers to the surface features of an object, including height and texture.

These terms may be defined with additional language in the remaining portions of the specification.

DETAILED DESCRIPTION

As shown in FIG. 1, a hook component 20 and a loop component 22 can be brought together to be releasably attached, or releasably engaged, to one another. The hook component 20 has a number of individual hooks 24 protruding generally perpendicularly from a resilient hook backing material 26. Similarly, the loop component 22 has a number of individual loops 28 protruding generally perpendicularly from a resilient loop backing material 30. The individual hooks 24 and the individual loops 28, when brought into contact with one another, engage with one another, with the hooks 24 latching onto the loops 28, until forcibly separated, thereby pulling the hooks 24 out of the loops 28.

The individual loops 28 of the loop component 22 can be needled, stitched or otherwise projected through the loop backing material 30, which can suitably be made from a non-woven material. The individual loops 28 can suitably be made from a fibrous non-woven web such as a spunbond non-woven web, or a staple fiber carded web. Alternatively, the individual loops 28 can be made of yarn or tow. Once the loops 28 have been formed, fibers forming the loops can be anchored in place by bonding the fibers to the loop backing material 30 with heat and/or adhesives or any other suitable means. Such suitable loop components 22 are available from Velcro USA, of Manchester, N.H.

Figure 2:
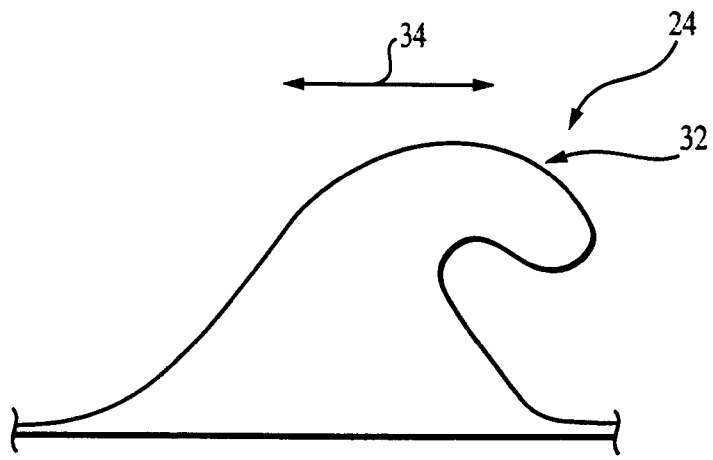
FIG. 2 is a front view of an individual hook of a hook component having a rounded free end.

The hook component 20 can include any of a number of improvements, or combinations thereof, to render the hook component 20 skin-friendly. Virtually any hook shape can be used. For example, the individual hooks 24 can have non-pointed free ends 32 to prevent poking of a wearer's skin. Individual hooks 24 having a simple, rounded free end 32 are known in the art. FIG. 2 shows an individual J-shaped hook 24 with a free end 32 rounded in the machine direction. The machine direction is indicated by an arrow 34 in FIGS. 1, 2, 6, 7, 10 and 11. Consequently, the term "cross-machine direction" refers to a direction normal to the machine direction. The cross-machine direction is indicated by an arrow 36 in FIGS. 3-5, 8 and 10.

Figures 3, 4, 5:
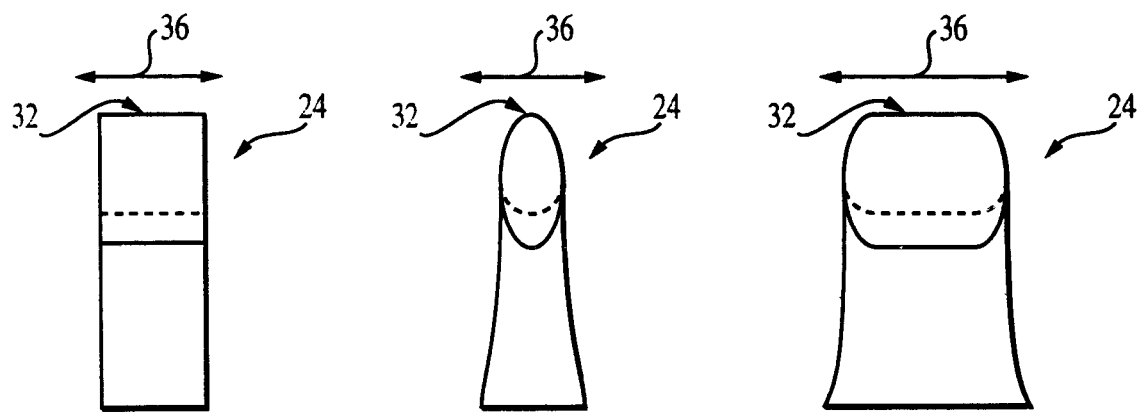
FIG. 3 is a side view of an individual hook of a hook component having at least one rounded free end.
FIG. 4 is a side view of an individual hook of a hook component having at least one rounded free end.
FIG. 5 is a side view of an individual hook of a hook component having at least one rounded free end.
Figure 24:
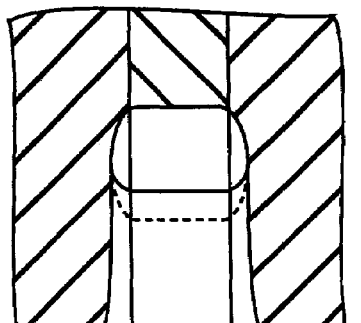
FIG. 24 is a cross-sectional view through a molding cavity for forming the wide hook of FIG. 5.

The free end 32 of the hook 24 shown in FIG. 2 is rounded in the machine direction and can be, but does not necessarily have to be, rounded in the cross-machine direction as well. FIG. 3 shows the hook 24 of FIG. 2 in the cross-machine direction, wherein the free end 32 of the hook 24 is not rounded in the cross-machine direction. FIG. 4 shows the free end 32 of the hook 24 of FIG. 2 as rounded in the cross-machine direction. A wide, rounded free end 32 renders the hook 24 more skin-friendly than current hooks having narrower widths, due to a greater area in contact with a wearer's skin. Individual hooks 24 having a large aspect ratio in an uppermost region of the hook 24, opposite the hook backing material 26, tend to be gentle on a wearer's skin because these large aspect ratios, particularly with rounded edges, do not poke the wearer the way pointed ends do. FIG. 5 shows the free end 32 of the hook 24 of FIG. 2 also rounded in the cross-machine direction and having a relatively large width, which can be molded in a cavity 102 spanning multiple adjacent mold rings, as shown in FIG. 24. The widths vary depending on over-all sizes of the hooks 24 and the loops 28.

Figure 6:
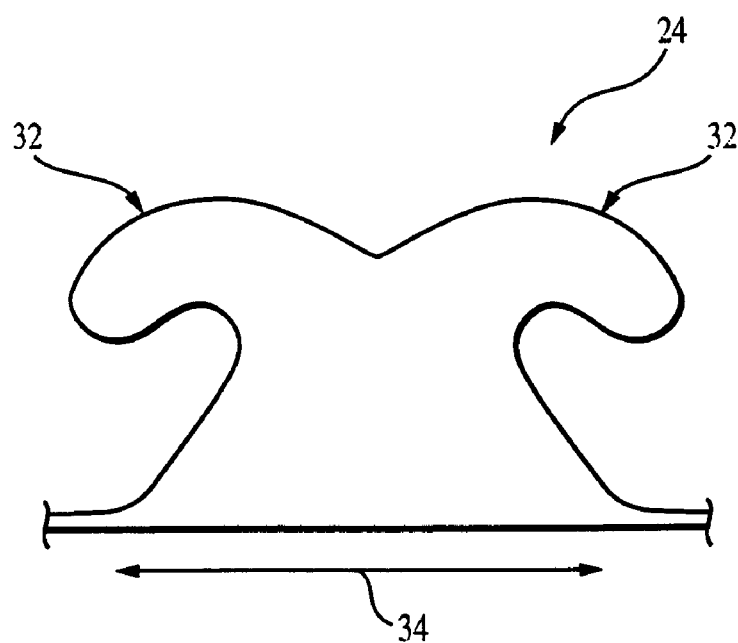
FIG. 6 is a front view of an individual hook of a hook component having two rounded free ends.

As shown in FIG. 6, the hook 24 can have more than one non-pointed free end 32. In this embodiment, the hook 24 has two rounded free ends 32 opposite one another. These two free ends 32 are rounded in the machine direction, as shown in FIG. 6, and can be non-rounded or rounded in the cross-machine direction, as shown in FIGS. 3-5.

Figure 7:
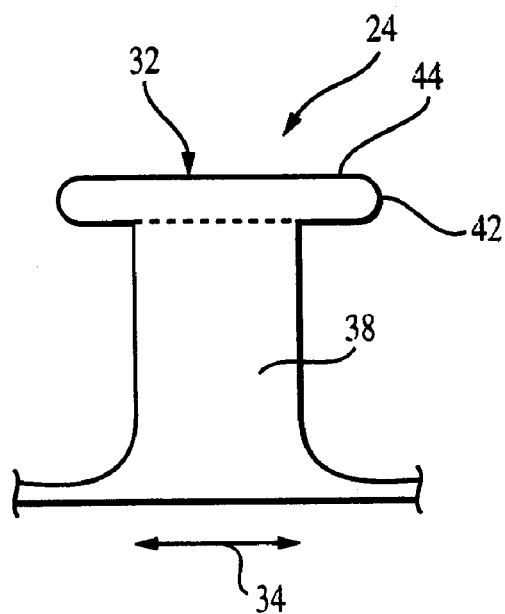
FIG. 7 is a front view of an individual hook of a hook component having a flat free end.
Figure 8:
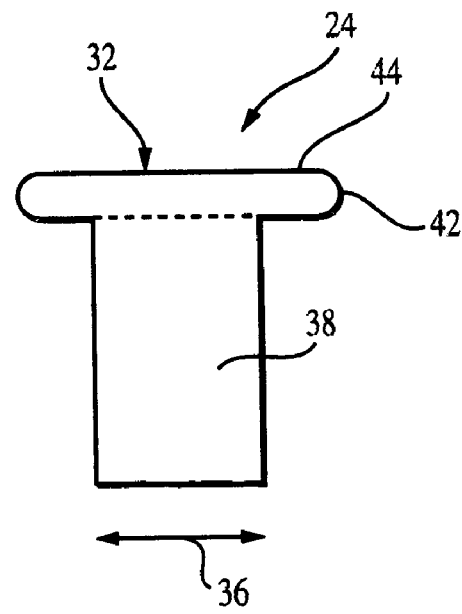
FIG. 8 is a side view of an individual hook of a hook component having a flat free end.

The term "non-pointed" free end 32 includes hooks 24 having a rounded free end, and also includes hooks 24 having a relatively flat free end 32, suitably with a rounded edge 42 about a top surface 44 of the flat free end. A mushroom-shaped hook 24 having a flat free end 32 is shown in FIG. 7. The hook 24 in this embodiment can look the same in the machine direction (FIG. 7) as in the cross-machine direction (FIG. 8), in which case a base portion 38 of the hook 24 is suitably round or square as viewed from above. Alternatively, the base portion 38 of the hook 24 can be oblong, rectangular, triangular, or any other suitable shape.

Figure 9:
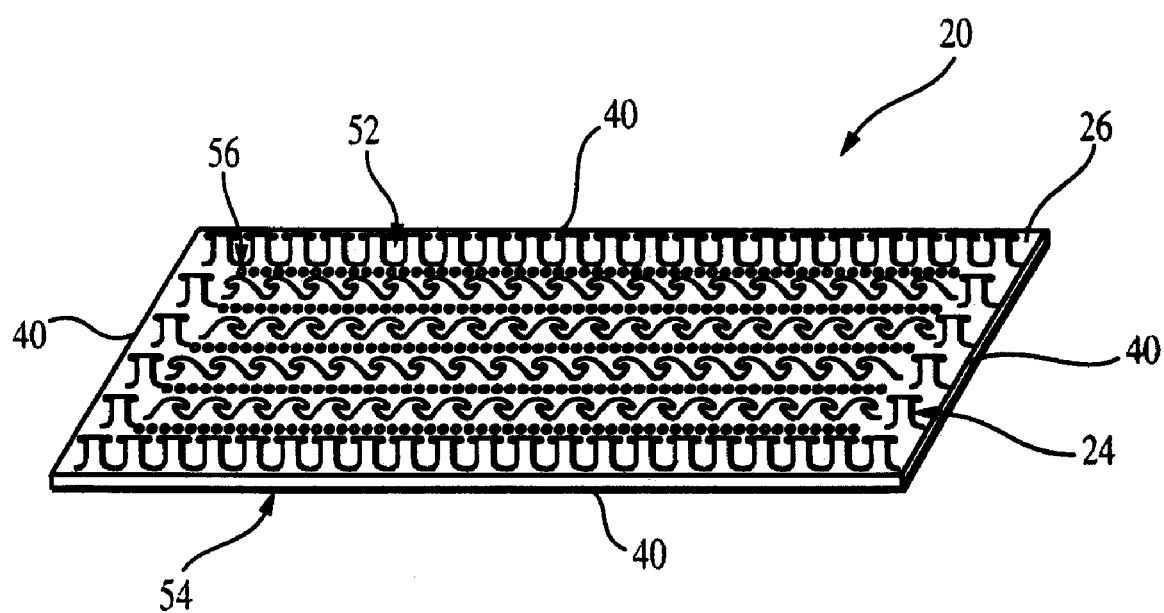
FIG. 9 is a perspective view of a hook component.

Referring to FIGS. 2-8, non-pointed free ends 32 on the hook component 20 reduce skin irritation by reducing any stress responses by the wearer due to a larger area in contact with a wearer's skin in comparison to a pointed free end. The embodiments shown in FIGS. 5-8 each have a particularly large aspect ratio in contact with a wearer's skin and are thus more skin-friendly than hooks 24 having a small aspect ratio. Individual hooks 24 having a large aspect ratio, such as non-pointed free ends 32, can be located across an entire surface of the hook component 20, or at least along an outer edge or edges 40 of the hook component 20 where the individual hook texture is most apparent to the wearer, as shown in FIG. 9.

Figure 10:
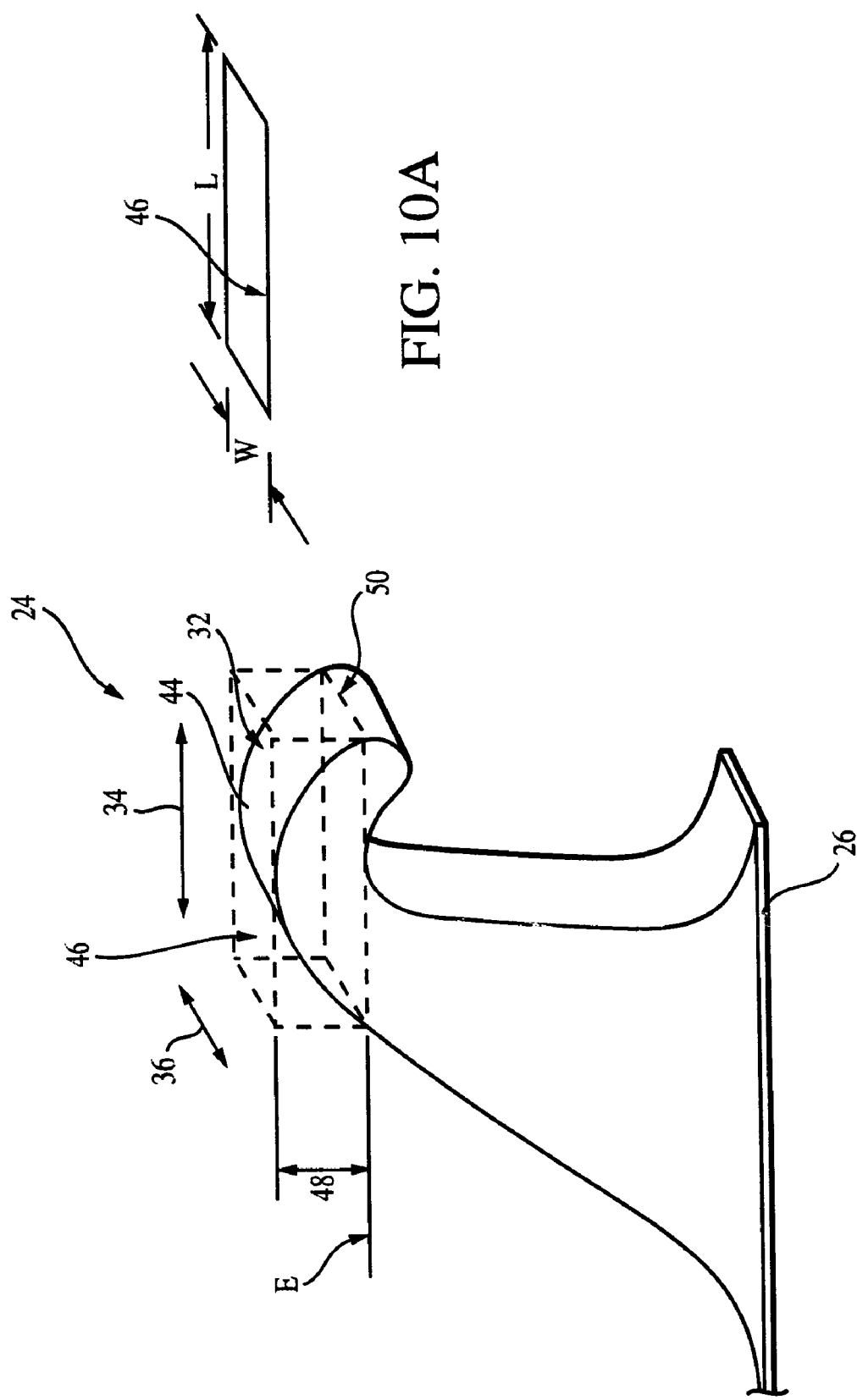
FIG. 10 illustrates the determination of the hook head size for calculating aspect ratio.

FIGS. 10 and 10A illustrate how the hook head area is determined for calculating the aspect ratio of the hook component. The head area is calculated at an elevation "E" corresponding to the maximum lateral overhang of the hook head at 50, as the area of the upper face 46 of the smallest parallelepiped (shown in dashed outline) having its base at "E" and parallel to backing 26, its front face intersecting maximum overhang point 50, and completely containing the portion of the hook head above elevation "E". As shown in FIG. 10A, the hook head area is the product of perpendicular dimensions "W" and "L". An individual hook 24 having a large head area in contact with a wearer's skin is more skin-friendly than an individual hook 24 having a small head area, such as a pointed end, in contact with a wearer's skin. Additionally, a hook component 20 having a high hook density, i.e., number of hooks per square centimeter, other factors being equal, is generally more skin friendly than a hook component 20 having a low hook density, also due to the greater aspect ratio. Thus, skin-friendliness can be achieved through individual hooks 24 having a large amount of area in contact with a wearer's skin, or a hook component 20 having a high hook density, or suitably, a hook component 20 having a high density of individual hooks 24 with each hook 24 having a large head area. Preferably, the aspect ratio of hook component 20 is in a range of 40 percent to 55 percent. More suitably, the aspect ratio of hook component 20 is in a range of 45 to 50 percent, and most preferably, about 47 percent.

Preferably, the point 50 of maximum overhang occurs at an elevation "E" that is very close to the most upper surface of the hook. Thus, it is preferable to minimize the penetration distance 48 for optimum skin-friendliness.

Skin-friendly hook components having an aspect ratio of greater than 40 percent can be achieved, as mentioned, through individual hooks 24 each having a large head area, particularly when in combination with a sufficiently large hook density. A hook density of 1000 to 2000 hooks per square inch (155 to 310 hooks per square centimeter) provides optimum spacing for a skin-friendly and useful hook component 20 for many garment applications. A hook density of 1200 to 1800 hooks per square inch (186 to 279 hooks per square centimeter) is even more preferred, and a hook density of 1300 to 1600 hooks per square inch (202 to 248 hooks per square centimeter) is most desirable. As indicated, high hook density results in a large aspect ratio, providing the feel of a nearly smooth texture. For example, hooks 24 having a relatively flat free end 32, as shown in FIG. 7, are particularly suitable for providing a smooth texture when closely spaced to one another on a hook component 20. The improved feel is understood to be at least in part because pressure exerted on a wearer's skin by the hook component 20 is more evenly distributed across a large area compared to a less dense arrangement of hooks 24.

Figure 11:
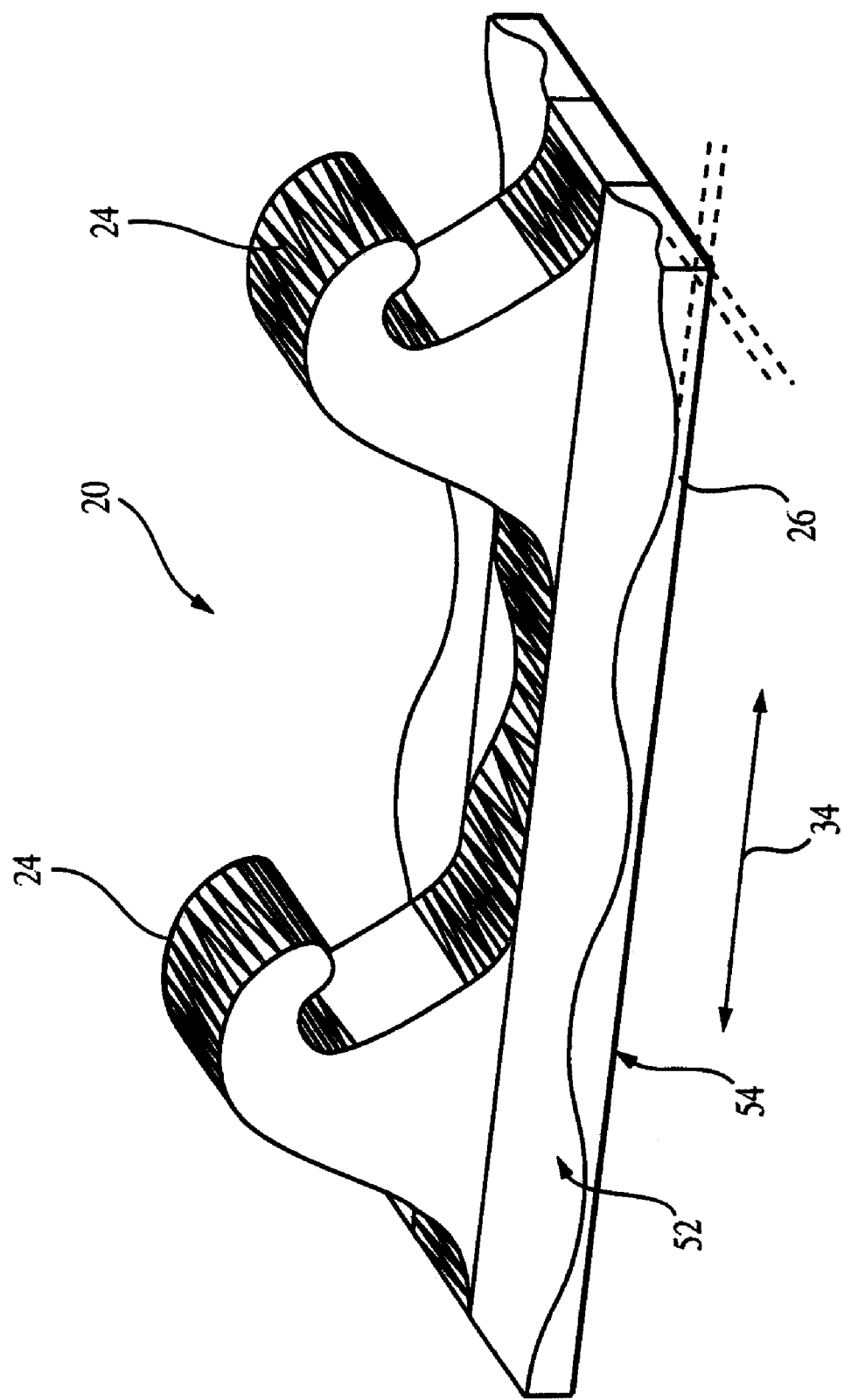
FIG. 11 is a perspective view of a hook component having a hook backing of varying thickness.

The hooks 24 are spatially arranged in rows on the hook backing 26. Flexibility of the hook backing 26 can be improved by changing the topography of the hook backing by varying the texture and/or thickness of the backing 26 along the surface of the backing 26. For example, the areas where the hooks 24 extend from the backing 26 can be thicker than areas between the hooks 24, thereby enabling the areas between the hooks 24 to bend with ease in response to force, or simply conform to a wearer's body. The thickness can be adjusted on either a top surface 52 of the hook backing 26, as shown in FIG. 11, or a bottom surface 54 of the hook backing 26, or on both the top and bottom surfaces 52, 54 of the hook backing 26. The thickness of backing 26 can also be adjusted by changing the texture of the backing 26 on either the top surface 52, the bottom surface 54 or both surfaces 52, 54. The texture can be patterned or somewhat random, and can be produced by using, for example, a patterned or knurled roll against which the backing 26 is pressed while in a pliable stage during the manufacturing process. In an alternative embodiment of the invention, hook backing 26 can be foraminous, with apertures 56 formed in the hook backing between individual hooks 24, as shown in FIG. 9. The apertures 56 lower the overall resistance of the backing to flexing and bending out of its plane.

The hook backing 26 suitably has a thickness ranging from a positive amount to 3.5 mils (88.9 microns), suitably 0.5 mil (12.7 microns) to 3.0 mils (76.2 microns), more suitably 1.0 mil (25.4 microns) to 2.5 mils (63.5 microns), with thickness varying across the surfaces 52, 54. More specifically, areas between the hooks 24 can have a thickness ranging from 0 mils (0 microns), i.e. apertures, to 3.0 mils (76.2 microns), suitably 0 mils (0 microns) to 2.5 mils (63.5 microns), more suitably 0 mils (0 microns) to 2.0 mils (50.8 microns), while the areas underneath and adjacent hooks 24 can have a thickness ranging from a positive amount to 3.5 mils (88.9 microns), suitably 0.5 mil (12.7 microns) to 3.0 mils (76.2 microns), more suitably 1.0 mil (25.4 microns) to 2.5 mils (63.5 microns). Furthermore, the edges 40 of hook backing 26 about a periphery of the hook component 20 may be suitably tapered to provide minimal resistance against a wearer's skin. The hook backing material 26 contributes toward skin-friendliness with its considerable flexibility and soft surface. More particularly, the considerable flexibility reduces stiffness along the edges 40 of the hook component 20, thereby further enhancing skin-friendliness.

The hooks 24 and the hook backing 26 are generally produced from the same material in one process. One suitable method of manufacture is the continuous molding method described by Fischer in U.S. Pat. No. 4,794,028, the contents of which are hereby incorporated by reference as if set forth in their entirety. In the Fischer process, the hook backing 26 and hooks 24 are simultaneously formed of a single continuous flow of molten resin, with the backing 26 formed under pressure in a nip adjacent a rotating mold roll having blind cavities in which the hooks 24 are molded, cooled and then released by stripping the cooled backing from the mold roll after leaving the nip. The mold roll is typically made of many circular mold plates each having hook-shaped notches cut through at their perimeters for molding a continuous row of hooks. The mold plates are alternated with solid spacer plates that form the flat lateral sides of the hook cavities. The hook 24 of FIG. 10 is illustrative of the flat-sided hooks molded in such cavities. In some cases, the hook cavities do not extend completely through the mold plates, such that only one side of each hook is flat. In other cases, mold rings having aligned concave hook cavity surfaces are placed together such that the resulting hook cavities have curved lateral sides, for forming hooks as shown in FIGS. 4 and 5, for example.

Although the tooling required to mold flat-sided hooks is generally considered to be simpler and less expensive to form than tooling for curve-sided hooks, sharp edges at the intersection of the flat hook sides and the upper surface of such hooks have been found to detract from a desirably soft feel against skin. Thus, the improvements described herein are of particular advantage as applied to such hooks, and to molded hooks in general.

The process known in the art as "cut and stretch", in which a softened polymer is extruded through a die having an elongated base opening (for extruding backing 26) contiguous with multiple hook-profiled openings (for extruding longitudinal rails having desired hook profiles), is also suitable for forming hook components of some hook shapes. After extrusion, the extruded rails are slit transverse to the extrusion direction, and the extruded backing stretched in the extrusion direction to separate the slit rail segments to form rows of individual hooks. The backing may also be stretched in the direction perpendicular to the extrusion direction, to reduce the backing thickness and increase the lateral distance between neighboring hook rows.

The hooks 24 of the hook component 20 may be made of a highly flexible polymer, or polymers, thereby enabling the hooks 24 to flex and bend correspondingly with a wearer's movements. When made of a highly flexible polymer, free ends 32 of the hooks 24 are less likely to poke a wearer's skin, thereby irritating the skin, in comparison to hooks made of less flexible polymers. Hooks 24 made of a flexible polymer bend in response to pressure, thereby alleviating stresses that could lead to skin-reddening or other types of skin irritation. If made of a flexible polymer, hooks 24 bend under a minimum amount of vertical pressure. Suitably, the polymer or polymers used to make the hooks 24 have a bulk flexural modulus in a range of 7 kpsi (48 MPa) to 30 kpsi (207 MPa). More suitably, the polymer or polymers used to make the hooks 24 have a bulk flexural modulus in a range of 7 kpsi (48 MPa) to 25 kpsi (173 MPa). Most suitably, the polymer or polymers used to make the hooks 24 have a bulk flexural modulus in a range of 7 kpsi (48 MPa) to 15 kpsi (104 MPa).

Suitable flexible polymers for the hooks 24 include elastomeric thermoplastic polymers made from block copolymers such as polyurethanes, copolyether esters, polyamide polyether block copolymers, polyester block amide copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Commercial examples of suitable elastomeric copolymers are those known as KRATON® materials which are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Other useful elastomeric materials include polypropylene, polyethylene, and polyurethane elastomeric materials. Examples of such polyurethane elastomeric materials include those available under the trademarks ESTANE® from B. F. Goodrich & Co. and MORTHANE® from Morton Thiokol Corp., polyester elastomeric materials such as those available under the trade designation HYTREL® from E.I. du Pont de Nemours & Company of Wilmington, Del., and those known as ARNITEL®, formerly available from Akzo Plastics of Arnhem, Holland and now available from DSM of Sittard, Holland.

Commercially available examples of thermoplastic elastomers based on polypropylene include SARLINK®, available from DSM Engineering Plastics, Evansville, Ind.; SANTOPRENE®, available from Advanced Elastomer Systems, Akron, Ohio; and UNIPRENE®, available from Teknor Apex, Pawtucket, R.I. ESCORENE® PD-3445, available from Exxon Chemical Co., Houston, Tex., is another flexible polypropylene but is not elastomeric.

Metallocene catalyzed polymers are another type of material suitable for hooks 24. A relatively new class of polymers, metallocene catalyzed polymers have excellent elasticity, and a narrow polydispersity number, e.g., Mw/Mn is 4 or less and may be produced according to the metallocene process. The metallocene process generally uses a catalyst that is activated, e.g., ionized, by a co-catalyst.

Metallocene process catalysts include bis(n-butylcyclopentadienyl) titanium dichloride, bis(n-butylcyclopentadienyl)zirconium dichloride, bis(cyclo-pentadienyl)scandium chloride, bis(indenyl)zirconium dichloride, bis(methylcyclo-pentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-fluorenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al., also assigned to Dow.

The hook backing 26 may be made from the same flexible polymers listed above as suitable for the individual hooks 24. A co-extrusion or layered extrusion process can be employed to form the individual hooks and the backing from different polymers in the same process.

Hooks 24 may be formed in a wide range of sizes. Preferably, the hooks have an overall height in a range of about 0.033 to 0.51 centimeter, and a maximum lateral head dimension of about 0.025 to 0.033 centimeter.

A skin-friendly hook component 20 results from many combinations of the disclosed features. For example, an advantageous hook component 20 can have a relatively large aspect ratio, and/or a flexible hook backing 26, and/or can be made of a flexible polymer. The improved flexibility of both the hook backing material 26 and the individual hooks 24 contributes to a soft, smooth texture of the hook component 20. Furthermore, a flexible hook backing 26 enables hooks 24 made of a flexible polymer to bend in response to minimum pressure, thereby reducing the threat of irritation to a wearer, yet provides enough room between the hooks 24 to enable the hooks 24 and the loops 28 to engage one another.

We have also realized that subjective personal impressions of the roughness of the feel of hook tape is affected by the extent to which the skin and its underlying tissue conforms about a particular feature. The more the structure and arrangement of the surface features allow the skin to conform about them, the greater the perception that the surface is "rough" or "abrasive", or that the subject has been "poked" by the feature in question.

FIGS. 12 and 12A illustrate how the arrangement of hooking members in a given array can affect the feel of the hook tape. In the tape 60 of FIG. 12, J-shaped hooking members 62 (each shown as a rectangle with an arrow facing toward the tip of the hooking member) are aligned in transverse rows with open base areas between the rows. One open base area 64 is shown in dashed outline for illustration. Because this open space 64 is unrestricted in the transverse direction, contacting skin penetrates deeper into the array of hooking members than in the array of hooking members on the hook tape 66 of FIG. 12A. The longitudinal distance "$d_L$" between adjacent hooking members 60 in each row is 0.030 inch in both FIG. 12 and FIG. 12A. Reducing "$d_L$" will also reduce skin conformance, but can also reduce hook performance. In the improved hook tape of FIG. 12A, conformance is also restricted in the transverse direction by hooking members 60 of adjacent, staggered rows. While actual skin penetration will be at least a combined second order function of the longitudinal and transverse dimensions of any open space between hooking members, the area of the largest internal open space is one approximate indication of the perceived roughness of the hook array. For reasonable feel quality, the maximum bounded open area or courtyard 68 within an array of hooking members is preferred to be less than about 0.010 square inch (more preferably, les than about 0.005 square inch, and even more preferably, less than about 0.001 square inch).

FIG. 13 shows how the edge row of hooks 62 in a traditional hook tape 60 results in rather poor skin conformance at the edge of the hook tape. A finger 70 is shown moving across the hook tape from its edge, significantly indented by the exposed upper edge of the outer row of hooks 62.

To reduce this effect and thereby improve the feel of the hook tape, the hook tape 72 of FIG. 14 is provided with three rows of edge transition elements 74 of staggered height, with an outer row of quite short elements 74, a second row of slightly larger elements, and so forth, such that the contacting skin surface 70 is gently guided up to the functional hooking members 62 without significant indentation. While the edge transition elements 74 of FIG. 14 are shown as having flat, horizontal upper surfaces, other element shapes can be employed to further reduce roughness. For example, the tape of FIG. 15 has elements 74' with tapered upper surfaces 76 that are inclined toward the adjacent edge of the hook tape. These and other shapes of transitional elements can be provided on the hook tape at very little cost, molded along with the hooking elements in the Fischer process by incorporating molding rings with appropriately configured cavities, arranged between adjacent spacer plates as are the hooking element molding rings. Such molded edge transition elements 74 may be hump-shaped, for example. Alternatively, standard hook tape with full-height hooking elements along the edge can be modified after molding to transform the outer few edge rows of hooking elements along each side into height-staggered transitional elements, such as by passing the hook tape edge under a heated, tapered roller.

Figure 18:
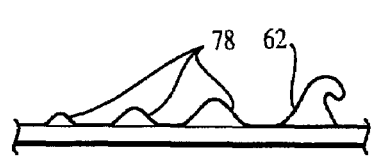
FIG. 18 also shows end transitional features near a hook member.

The ends of a cut section of hook tape can be provided with similar transition elements, as end transition elements along the end edge of the cut section. FIG. 16 shows how, particularly with J-hook or palm tree hooking members with exposed tips facing the end of the section of tape, contacting skin 70 can be "poked" by the edge row of hooking members. As shown in FIGS. 17 and 18, our improved hook tape is equipped with three rows of molded, hump-shaped end transition elements 78 at either end, helping to ease the transition of the contacting skin up onto the array of functional hooking members 62. Molding such end transition elements 78 in a traditional Fischer molding process in which the hooking members face in the machine directions requires modified hooking member mold rings with end transition element cavities positioned at predetermined positions about their periphery. Furthermore, the transverse cutting of such a molded tape into sections for use, for example, on diaper tabs, must be controlled to sever the hook tape at the proper location with respect to the molded end transition elements. A preferred alternative is to transform the functional hooking members 62 adjacent a transverse cut as the tape is cut into sections. For example, the cutting mechanism can be equipped with heated, tapered flanges for permanently deforming the adjacent hooking elements.

Figure 19:
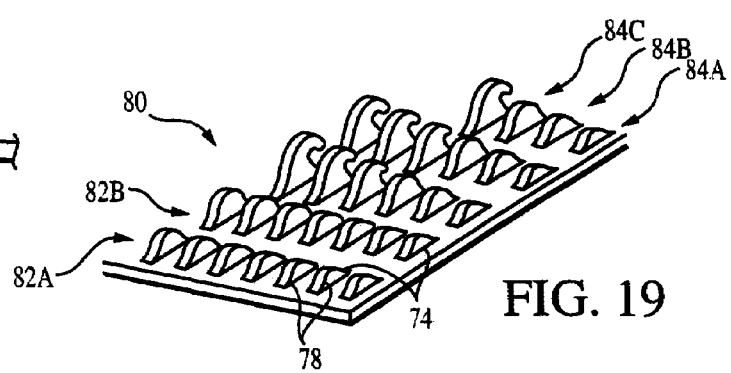
FIG. 19 is a perspective view of an improved hook tape section having both end and edge transition features.

Both edge and end transition elements can be used to advantage on a single section of hook tape, as illustrated in FIG. 19. In this embodiment, tape 80 has two end rows 82A and 82B of end transition elements 78, and three edge rows 84A, 84B and 84C of edge transition elements 74. It is noted that a single structure may function both as an end transition element and an edge transition element.

Figure 20:
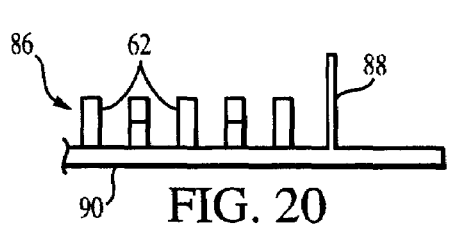
FIG. 20 is an end view of a hook tape having an edge skirt.
Figure 20A:
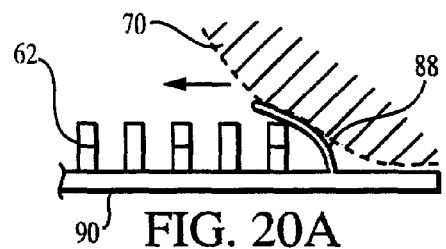
FIG. 20A is an end view illustrating skin contact with the longitudinal edge of the hook tape of FIG. 20.
Figure 21:
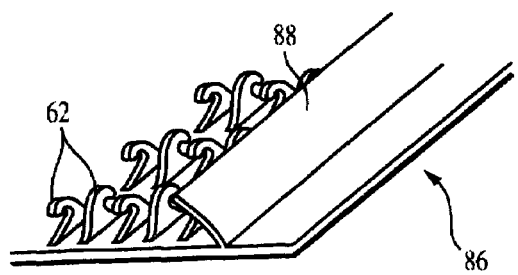
FIG. 21 is a perspective view of the hook tape of FIG. 20.

FIGS. 20 and 21 shows another means for improving the edge comfort of molded hook tape. Hook tape 86 is equipped with a longitudinally continuous, integrally molded skirt 88 extending from base 90 between the longitudinal edge of the base and the array of hooking members 62. As a skin surface 70 moves into the hook array from the edge of the tape (FIG. 20A), skirt 88 is deflected to drape over the edge row of hooking members and reduce perceived roughness. During normal engagement with a mating surface (e.g., a loop member), skirt 80 is thin enough to buckle or be otherwise readily displaced so as to not significantly interfere with the fastening.

Figure 22:
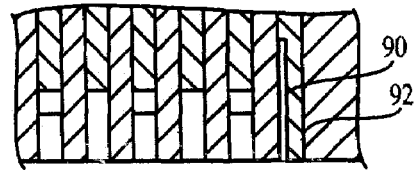
FIG. 22 is a cross-section of a portion of a mold roll configured to form the hook tape of FIG. 21.

Skirt 88 can be integrally molded, for example, in a channel 90 defined within a skirt-molding ring 92 of a Fischer-type mold roll, as shown in FIG. 22. Preferably, such a channel 90 is slightly tapered for easy stripping of the molded hook tape.

Figure 23:
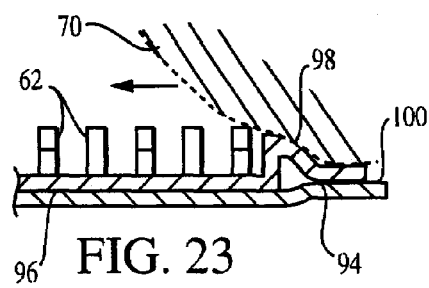
FIG. 23 is a longitudinal cross-section through a diaper tab having a section of improved hook tape secured across the tab, the hook tape including a continuous edge guard.

The molded hook tape 94 of FIG. 23 has a base 96 that, along its longitudinal edge, is molded to have a continuous rib 98 extending alongside the array of hooking members 62. Rib 98 may be molded as a discontinuity in the otherwise planar base 96, such as by molding the base in a nip (not shown) between a molding roll defining a V-shaped rib-forming channel, and a pressure roll with a V-shaped protrusion extending into the channel. With a section of the molded hook tape 94 secured to a diaper tab 100 as shown, rib 98 forms a flexible cushion to help to transition the skin 70 onto the array of hooking members. The open ends of the cushion can later be closed down against the diaper tab, such as with a hot, tapered iron that can be employed to simultaneously form end transition members of molded end hooking members of the tape, as discussed above.

As an alternative to molding the hook tape base 90 to have a V-shaped discontinuity 98, as shown, the tape base may be molded with three spaced, longitudinal grooves (not shown) to serve as living hinges to enable the hook tape to be pleated as it is secured to the diaper tab to form rib 98.

It will be appreciated that details of the foregoing embodiments, given for purposes of illustration, are not to be construed as limiting the scope of this invention. Although only a few exemplary embodiments have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A hook component for use with a mating loop component for hook and loop fastening, the hook component including a hook backing and a plurality of hooks arranged in an array and protruding from one side of the hook backing to a nominal height, wherein
   the hook component further includes at least two rows of edge transition members protruding from the backing between one longitudinal edge thereof and the array of hooks, the edge transition members being of a height less than the nominal height of the hooks and the edge transition members of an outer row being of a lesser height than the edge transition members of an inner row disposed between the hooks and the outer row of edge transition members.

2. The hook component of claim 1, comprising three rows of edge transition members protruding from the backing between the longitudinal edge and the array of hooks, the edge transition members of each row being taller than the members of any transition members closer to the longitudinal edge.

3. The hook component of claim 1, wherein the edge transition members are of molded form.

4. The hook component of claim 1, wherein the edge transition members have upper surfaces angled away from said longitudinal edge.

5. An absorbent article comprising the hook component of claim 1.

6. A diaper comprising the hook component of claim 1.

7. A training pant comprising the hook component of claim 1.

8. A feminine hygiene product comprising the hook component of claim 1.

9. An incontinence product comprising the hook component of claim 1.

10. A medical garment comprising the hook component of claim 1.

11. A hook component for use with a mating loop component for hook and loop fastening, the hook component including an elongated hook backing and a plurality of hooks arranged in an array and protruding from one side of the hook backing to a nominal height, wherein
   the hook component further includes at least two rows of end transition members protruding from the backing between one end thereof and the array of hooks, the end transition members being of a height less than the nominal height of the hooks and the end transition members of an outer row being of a lesser height than the end transition members of an inner row disposed between the hooks and the outer row of end transition members.

12. The hook component of claim 11 comprising three rows of end transition members protruding from the backing between said end of the backing and the array of hooks, the end transition members of each row being taller than the members of any transition members closer to said end of the backing.

13. The hook component of claim 11, wherein the end transition members are of molded form.

* * * * *